US008576395B2

(12) United States Patent
Babico et al.

(10) Patent No.: US 8,576,395 B2
(45) Date of Patent: *Nov. 5, 2013

(54) INTEGRATED MICROBIAL COLLECTOR

(71) Applicant: BioVigilant Systems, Inc., Tucson, AZ (US)

(72) Inventors: John Y. Babico, Tucson, AZ (US); Jian-Ping Jiang, Tucson, AZ (US)

(73) Assignee: Azbil Biovigilant, Inc., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/739,730

(22) Filed: Jan. 11, 2013

(65) Prior Publication Data
US 2013/0130368 A1   May 23, 2013

Related U.S. Application Data

(63) Continuation of application No. 12/642,722, filed on Dec. 18, 2009, now Pat. No. 8,358,411.

(60) Provisional application No. 61/138,878, filed on Dec. 18, 2008.

(51) Int. Cl.
G01N 21/00 (2006.01)
G01N 15/02 (2006.01)
C12Q 1/04 (2006.01)
C12M 1/34 (2006.01)

(52) U.S. Cl.
USPC ........ 356/335; 356/336; 356/338; 435/288.7; 435/34

(58) Field of Classification Search
USPC ............... 356/335–343, 72–73, 317, 218; 250/461.1, 461.2, 458.1, 286, 287; 436/164; 435/288.7
See application file for complete search history.

(56) References Cited

U.S. PATENT DOCUMENTS

| 4,734,372 | A | * | 3/1988 | Rotman | ........................ 435/29 |
|---|---|---|---|---|---|
| 5,646,597 | A | | 7/1997 | Hamburger et al. | |
| 5,969,622 | A | | 10/1999 | Hamburger et al. | |
| 5,986,555 | A | | 11/1999 | Hamburger et al. | |
| 6,008,729 | A | | 12/1999 | Hamburger et al. | |
| 6,087,947 | A | | 7/2000 | Hamburger et al. | |
| 6,532,067 | B1 | | 3/2003 | Chang et al. | |
| 6,806,464 | B2 | | 10/2004 | Stowers et al. | |
| 6,936,828 | B2 | | 8/2005 | Saccomanno | |
| 7,009,189 | B2 | | 3/2006 | Saccomanno | |
| 7,057,712 | B2 | | 6/2006 | Beck et al. | |
| 7,126,687 | B2 | | 10/2006 | Hill et al. | |
| 7,224,852 | B2 | | 5/2007 | Lipton et al. | |
| 7,298,478 | B2 | | 11/2007 | Gilbert et al. | |
| 7,410,809 | B2 | | 8/2008 | Goix et al. | |
| 7,430,046 | B2 | | 9/2008 | Jiang et al. | |

(Continued)

FOREIGN PATENT DOCUMENTS

JP     01312991 A  * 12/1989

*Primary Examiner* — Sang Nguyen
(74) *Attorney, Agent, or Firm* — Michael Curley Quarles & Brady LLP

(57) ABSTRACT

A system for real-time sizing of fluid-borne particles is disclosed. The system further determines, in real time, whether the detected particles are biological or non-biological. As the fluid is being tested, it is exposed to a microbe collection filter which is cultured to determine the type of microbes present in the fluid being tested.

14 Claims, 6 Drawing Sheets

(56) References Cited

U.S. PATENT DOCUMENTS

| | | | |
|---|---|---|---|
| 7,932,490 B2* | 4/2011 | Wang et al. | 250/287 |
| 2004/0057050 A1 | 3/2004 | Beck et al. | |
| 2004/0079651 A1 | 4/2004 | Kober et al. | |
| 2004/0161143 A1 | 8/2004 | Dietz et al. | |
| 2004/0171137 A1 | 9/2004 | Powers et al. | |
| 2005/0266516 A1 | 12/2005 | Kanipayor et al. | |
| 2006/0079000 A1 | 4/2006 | Floriano et al. | |
| 2009/0060798 A1* | 3/2009 | Williams et al. | 422/111 |

* cited by examiner

INTEGRATED MICROBIAL COLLECTOR

CROSS-REFERENCE TO RELATED APPLICATION

This is a Continuation Application which claims priority from U.S. Non-Provisional Application having Ser. No. 12/642,722, filed on Dec. 18, 2009, to issue as U.S. Pat. No. 8,358,411, which in turn claims priority to U.S. Provisional Application having Ser. No. 61/138,878, filed Dec. 18, 2008. The contents of each of these applications are entirely incorporated herein by reference in their entirety, for all purposes.

FIELD OF INVENTION

The present invention relates to generally to a system and method for detecting airborne or liquid-borne particles (generally, fluid-borne particles), and more particularly to a system and method for detecting airborne or liquid-borne particles, determining the size of the particles, determining the particles' status as biological or inert, and classifying the type of biologic particle detected.

BACKGROUND OF INVENTION

A variety of manufacturing environments require strict control over the presence of foreign debris in the air. Semiconductor manufacturing, for example, has long required "clean-rooms" that use extensive air filtering to reduce the number and size of particles in the air to some acceptable level. Other manufacturing environments have similar but distinct requirements. For example, in pharmaceutical or medical device manufacturing environments it is critical to control not only the number of particles in the air, but minimization of biologic particles is of particular importance. Microbial contamination, for example, can render an entire batch of pharmaceutical product unusable leading to significant monetary losses in the manufacturing process. Additionally, it is advantageous to have instantaneous detection of contamination events, including instantaneous information about whether a contamination event is biologic or non-biologic, during the manufacturing process for pharmaceuticals or medical devices.

A variety of systems and methods exist that provide instantaneous detection of fluid borne particles. For example, certain detectors have been designed to detect fluid borne particles and provide warning when the number of particles within an air sample exceeds a predetermined minimum value. Exemplary devices are described in U.S. Pat. Nos. 5,646,597, 5,969,622, 5,986,555, 6,008,729, and 6,087,947, all to Hamburger et al. These detectors all involve direction of a light beam through a sample of environmental air such that part of the beam will be scattered by any particles in the air, a beam blocking device for transmitting only light scattered in a predetermined angular range corresponding to the predetermined allergen size range, and a detector for detecting the transmittal light. An alarm is actuated if the light detected at the detector is above a predetermined level.

Additionally, systems and methods exist that instantaneously determine whether detected particles are biologic or inert. For example, U.S. Pat. No. 7,430,046 to Jiang et al., discloses systems and methods for simultaneously measuring particle size by use of Mie scattering and determining whether the measured particles are biologic or inert by detecting fluorescence excited in certain biological chemicals present in the measured particles.

Although fluorescence analysis can, in certain cases, be used to determine the type of biologic particle detected, i.e., the type of organism, it would be advantageous to have additional systems and methods that could simultaneously collect information on particle size, whether a particle is biologic or non-biologic, and the type of biologic particle that has been detected.

SUMMARY OF THE INVENTION

Embodiments of the invention continuously sample fluid containing particles from an environment to be monitored. Sampled fluid is passed through a sampling area, where it is exposed to light. Light scattered by the particles in the fluid is detected and used to determine the size of the particles. Light emitted by fluorescence from the particles is also detected and used to determine whether the particles are biological or non-biological. A filter containing a gas-permeable substance to which microbes adhere, (i.e., a microbe collection filter) is placed after the sampling area, such that the microbe collection filter is placed into the flow of the fluid being measured. In certain embodiments, the filter is situated atop a circular support plate including perforations allowing fluid to flow through the plate. The microbe collection filter collects biological particles from at least a portion of the flow of fluid. After optical measurements have been performed for a predetermined amount of time, and microbe collection filter has been exposed, the filter is removed, microbial nutrients and/or water are added if necessary, and the filter is incubated and examined for the growth of organisms according to any of a number of means, e.g., colony counting, observing the macroscopic appearance of the growth patterns of microbes on the filter, microscope observation of the microbes or chemical testing for the metabolic by-products of microbial growth.

In one embodiment, a microbial detection and identification system is described. The system includes a sampling area including a fluid, a light source, a first optical detector and a second optical detector. The system further includes a microbe collection filter in fluid communication with the sampling area. The light source illuminates particles in the sampling area, the first detector detects light scattered into a predetermined angular range by particles of a predetermined size, and the second detector measures light emitted by fluorescence from illuminated biological particles in the sample area. Additionally, the fluid is exposed to the microbe collection filter causing particles in the fluid to adhere to the microbe collection filter.

In certain embodiments, a first optical system directs scattered light from the sampling area to the first detector and a second optical system that directs fluorescence light from the sampling area to the second detector. In certain embodiments, the second optical system includes a long-pass filter that selectively transmits light having a wavelength of light emitted by fluorescence by illuminated particles in the sample area. In certain embodiments, an ellipsoidal reflector is included having a first focus at the sampling area and a second focus near the second detector.

In certain embodiments, the long-pass optical filter comprises two long-pass reflective filters in series. In certain embodiments, the light source comprises an LED or a diode laser, and the light source emits at a wavelength of approximately between 350 nm and 410 nm. In certain embodiments, the microbe collection filter includes a first surface, a second surface, and a gas permeable interior allowing the fluid to flow into the first surface, and out of the second surface. In certain embodiments, the microbe collection filter is gelatin.

In some embodiments, the fluid is air, and additional embodiments include a blower in fluid communication with the sampling area, where the blower supplies negative pressure to the sampling area thereby drawing environmental air into the sampling area and evacuating air from the sampling area as it is optically measured. In certain embodiments, the blower is in fluid communication with the microbe collection filter, and air is drawn through the microbe collection filter after it is optically measured.

Certain embodiments recite a method of detecting microbial contamination in a fluid. The method involves illuminating a fluid with a light source, detecting particles of a predetermined size range present in the fluid by measuring light scattered by illuminated particles into a predetermined range of angles, classifying particles in the fluid as biological or non-biological by measuring fluorescent light emitted from illuminated particles, and exposing a microbe collection filter to the fluid.

Certain embodiments include storing data related to the detection of particles of a predetermined size range and classification of particles as biological or non-biological for further analysis. Additional embodiments include culturing the exposed microbe collection filter. Other embodiments include analyzing the cultured exposed microbe collection filter to determine the types of microbes present on the microbe collection filter at the time of exposure.

Certain embodiments include analyzing the cultured exposed microbe collection filter comprises one or more of: colony counting, observing the macroscopic appearance of the growth patterns of microbes on the cultured exposed microbe collection filter, microscope observation of microbes on cultured exposed microbe collection filter, and chemical testing for the metabolic by-products of microbial growth present on the cultured exposed microbe collection filter. Other embodiments include storing data related to the detection of particles of a predetermined size range and classification of particles as biological or non-biological for further analysis. Certain embodiments include correlating the determination of the types of microbes present on the microbe collection filter at the time of exposure with stored data related to size of particles present in the fluid at the time of exposure and the status of the particles as biological or non-biological.

Certain embodiments include a method of characterizing a contamination event. The method involves illuminating a first fluid with a light source, detecting particles of a pre-determined size range present in the first fluid by measuring light scattered by illuminated particles into a predetermined range of angles, and classifying particles in the first fluid as biological or non-biological by measuring fluorescent light emitted from illuminated particles. The method also includes, storing data related to a scattering and fluorescence characteristics of particles in the first fluid, exposing a microbe collection filter to the first fluid, culturing the microbe collection filter and analyzing the cultured exposed microbe collection filter to determine the types of microbes present on the microbe collection filter at the time of exposure. The method also includes correlating the determination of the types of microbes present on the microbe collection filter at the time of exposure with stored data related to the scattering and fluorescence characteristics of particles in the first fluid, optically detecting scattering and fluorescence characteristics of particles in a second fluid, and comparing the detected scattering and fluorescence characteristics in the second fluid with the stored data related to the scattering and fluorescence characteristics of particles in the first fluid. Other embodiments are directed to a method where on the basis of the comparison, determining that microbes present in the first fluid are likely present in the second fluid.

Advantages of the invention include the ability to perform instantaneous, simultaneous particle sizing and detection of biological or non-biological organisms. Additional advantages include the ability to determine the type of biological particle detected and correlate data on the type of organism detected with the real-time particle data to fully characterize a contamination event. Additional advantages include the possibility of predicting the type of microbial contamination associated with future events on the basis of past correlations between optical and growth-medium measurements of particles.

BRIEF DESCRIPTION OF THE DRAWINGS

Implementations of the invention will become more apparent from the detailed description set forth below when taken in conjunction with the drawings, in which like elements bear like reference numerals.

DETAILED DESCRIPTION OF THE INVENTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow charts included are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
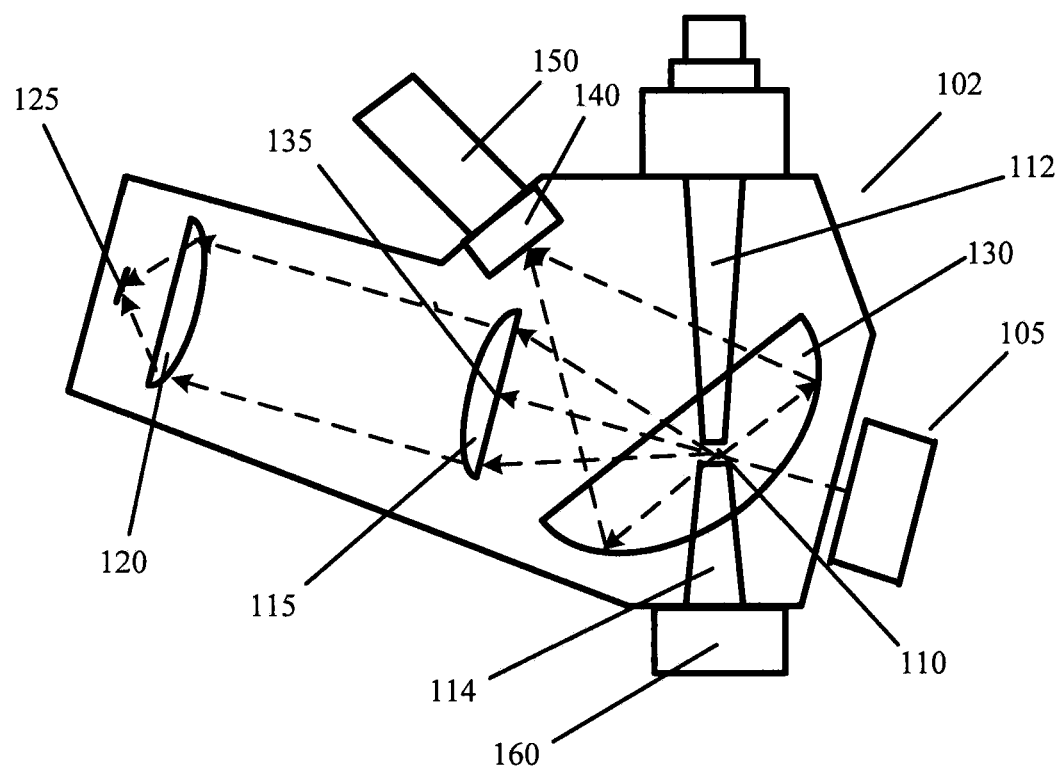
FIG. 1 is a schematic diagram of a system for instantaneous and simultaneous particle sizing and biological detection according to an embodiment of the invention.

FIG. 1 shows a system for instantaneous particle sizing and biological particle detection according to an embodiment of the invention. The system of FIG. 1 includes a housing 102, which serves to seal and/or isolate the interior components of the system from contamination from the surrounding air and interference from light sources in the environment of the system.

The system of FIG. 1 further includes a light source 105. In one embodiment, light source 105 produces an output having a wavelength between 270 nm and 410 nm. In one embodiment, light source 105 produces an output having a wavelength between 350 nm and 410 nm. In one embodiment, light source 105 produces an output having a wavelength of about 405 nm. The spectral characteristics of light source 105 are such that light emitted by light source 105 is capable of undergoing Mie scattering when interacting with particles of a size range of interest. Additionally, light source 105 is selected to have a wavelength capable of exciting intrinsic fluorescence from metabolites inside microbes and other biological particles. A wavelength of about 270 nm to 410 nm is chosen based on the observation that microbes and biological particles contain at least one of a number of primary metabolites that exhibit fluorescence: tryptophan, which normally fluoresces at excitation wavelengths of about 270 nm, with a range of about 220 nm to about 300 nm; nicotinamide adenine dinucleoetide (NADH), which normally fluoresces at excitation wavelengths of about 240 nm, with a range of about 320 nm to about 420 nm; and riboflavin, which normally fluoresces at wavelengths of about 200 nm, with a range of between 320 nm to about 420 nm. In the case of bacterial endospores, dipicolinic acid (DPA) normally fluoresces at excitation wavelengths of about 400 nm, with a range of about 320 nm to about 420 nm. A light source having a wavelength output of about 350 nm to about 410 nm ensures excitation of two of the three aforesaid primary metabolites: NADH and riboflavin, as well as DPA. Selection of this wavelength band allows for fluorescence to be generated and detected in bioparticles, but excludes excitation of non-biological sources of florescence such as diesel engine exhaust and other inert particles such as dust or baby powder.

Light source 105 can be a laser such as a diode laser, an LED or a spectrally filtered broadband source such as a lamp. Light source 105 can optionally include collimating or beam shaping optics to produce a substantially collimated output and/or an output having a transverse beam profile that is flat, in terms of power. Optionally, light source 105 includes an optical fiber that delivers light to the vicinity of the other elements of the system of FIG. 1. When an optical fiber is used to deliver light from a remotely situated light source, collimating or beam shaping optics may optionally be provided at the output of the optical fiber.

Light source 105 provides a substantially collimated beam of light to at least a portion of the sampling area 110. The intersection of the substantially collimated beam from light source 110 and the sampling area creates an interrogation zone, which is an illuminated portion of the sampling area. In one embodiment, where the fluid to be measured is air or some other gas, sampling area 110 is defined by the space between two air nozzles that provide air flow through the sampling area. In the embodiment of FIG. 1, sampling area 110 is defined by the space between two nozzles, an entrance nozzle 112, which supplies air to the sampling area, and an exit nozzle 114, which extracts air from the sampling area.

Upon illumination from light source 105, particles within sampling area 110 scatter light by Mie scattering. Mie scattering generally scatters light at angles inversely proportional to particle size. Accordingly, relatively small particles will scatter light at higher angles relative to the scattering produced by relatively larger particles. In practice, scattered light emerges from sampling area 110 in a cone centered about an axis defined by the collimated beam emerging from light source 105. The amount of light scattered into various angles is used, according to certain embodiments of the invention, to determine the size of the particles scattering light.

The system of FIG. 1 further includes a scattered light collection lens 115. In one embodiment, scattered light collection lens is a plano-convex lens arranged with the plano side facing toward sampling area 110 to minimize the spherical aberration associated with collecting and collimating scattered light. Scattered light collection lens 115 collects and collimates light scattered at relatively high angles by particles in sampling area 110 by being configured and positioned such that its front focal plane is co-incident with sampling area 110.

The system of FIG. 1 further includes a scattered light condenser lens 120. Scattered light condenser lens 120 takes collimated light emerging from scattered light collection lens 115 and focuses that light onto scattered light detector 125, which generates an electrical signal in proportion to the amount of scattered light incident on detector 125. In one embodiment, scattered light detector 125 is a photo-diode.

The system of FIG. 1 further includes beam blocking device 135. Beam blocking device 135 prevents further propagation of the collimated beam emitted by light source 105 after light emitted by light source 105 has propagated through sampling area 110. In one embodiment, beam blocking device 135 is a disk of optically absorptive material of a diameter somewhat greater than the beam diameter of the collimated beam emitted by light source 105. In the embodiment of FIG. 1, beam blocking device 135 is affixed to scattered light collection lens 115. In certain embodiments, beam blocking device 135 is a disc of black anodized aluminum. In other embodiments, beam blocking device 135 is a small light box with an absorptive interior coating arranged to force light emitted by light source 105 and entering the light box to undergo multiple internal reflections. Alternatively, beam blocking device is a fold mirror that directs light emitted by light source 105 to a beam dump arranged at some position outside of the optical components pictured. Alternatively, beam blocking device 135 is a conical shape with an absorptive interior coating that the beam enters at the open side. Beam blocking device 135 can be any device or combination of devices that prevents further propagation of the collimated beam, or stray reflections caused by the collimated beam, emitted by light source 105 after light emitted by light source 105 has propagated through sampling area 110.

The scattered light detection components of the system of FIG. 1 are arranged such that only a specific range of angles of scattered light are detected by scattered light detector 125. This can be accomplished in a number of ways. For example, the scattered light collection components can be sized and/or positioned in such a way as to only intercept light that has been scattered into a predetermined angular range of interest. Beam blocking device 135 inherently blocks very low angle light, including the unscattered light that passes through the sampling area 110 from light source 105. In one embodiment, beam blocking device 135 is sized to block not only light that is propagating along an optical axis defined by the beam from light source 105, but also light that is scattered at low, but still non-zero angles. In this way, in certain embodiments, beam blocking device 135 is used to define a lower bound for the range of angles measured by the scattered light measurement components.

In certain embodiments, an upper bound for the range of angles measured by the scattered light measurement components is established by the position and size of scattered light collection lens 115. Light scattered at high angles will not be intercepted by scattered light collection lens 115, so the size and distance of scattered light collection lens from the plane of sampling area 110 defines an upper bound for the range of angles measured by the scattered light measurement components. Additionally or alternatively, annular masks of optically non-transmissive material may be placed in the scattered light detection path, for example, on scattered light condenser lens 120 or the scattered light collection lens 115 to limit the range of scattering angles measured.

The system of FIG. 1 further includes an ellipsoidal reflector 130. The shape of ellipsoidal reflector 130 is defined with respect to a vertex located off the axis defined by the beam of substantially collimated light emitted by light source 105. In other words, when viewed with respect to the axis defined by light source 105, the collimated beam emitted by light source 105, sampling area 110 and the scattered light collection components, ellipsoidal reflector 130 is an off-axis ellipse. A first focus of ellipsoidal reflector 130 is located at the sampling area 110 and is substantially co-incident with the front focal point of scattered light collector lens 115. A second focus of ellipsoidal reflector 130 is located near the input port of a photomultiplier tube ("PMT") 150, the function of which is set forth in further detail below. In one embodiment, ellipsoidal reflector 130 includes a circular aperture, for example, near its vertex, to allow for uninterrupted propagation of light from light source 105 to sampling area 110.

Particles undergoing florescent emission within the sampling area 110 will emit light isotropically, that is, will emit equal optical power into all angles defining a sphere. Ellipsoidal reflector 130 is positioned such that it intercepts at least a portion of the light emitted by fluorescence from particles within the sampling area. The fluorescence light collected by parabolic reflector 130 at its first focus is directed along an axis defined by ellipsoidal reflector 130 toward the second focus located near an input port to PMT 150.

The system of FIG. 1 further includes back-to-back long-pass optical filters 140, i.e., two long-pass, reflective interference filters in series. In one embodiment, long-pass optical filters 140 are reflective interference type filters that transmit light having a wavelength longer than a certain wavelength while reflecting light having a wavelength shorter than a certain wavelength. The spectral characteristics of filters 140 are such that light emitted by particles within the sampling area 110 by fluorescence is transmitted, while light having substantially the same wavelength as that emitted by light source 105 is reflected.

Since fluorescence results in the emission of light having a longer wavelength than the excitation wavelength, filters 140 pass only light emitted by fluorescence, while reflecting noise (e.g., stray reflections) from the light source 105 as well as light scattered by particles within the sampling area 110 at angles toward PMT 150. Two long-pass filters are used in series to improve the performance of the filters. This arrangement is advantageous when placing the filters 140 in a converging beam, i.e., where the filters are used at non-zero angles of incidence.

The system of FIG. 1 further includes blower 160. Blower 160 is arranged to draw fluid in the sampling area out of the system after it has been optically interrogated.

It is important to note that the specifics of the optical collection systems for scattered and fluorescent light described above with respect to FIG. 1 are exemplary and not required. Any combination or configuration of optical system capable of simultaneously collecting and measuring scattered and fluorescent light should be deemed to be within the scope of embodiments of the invention.

Figure 2:
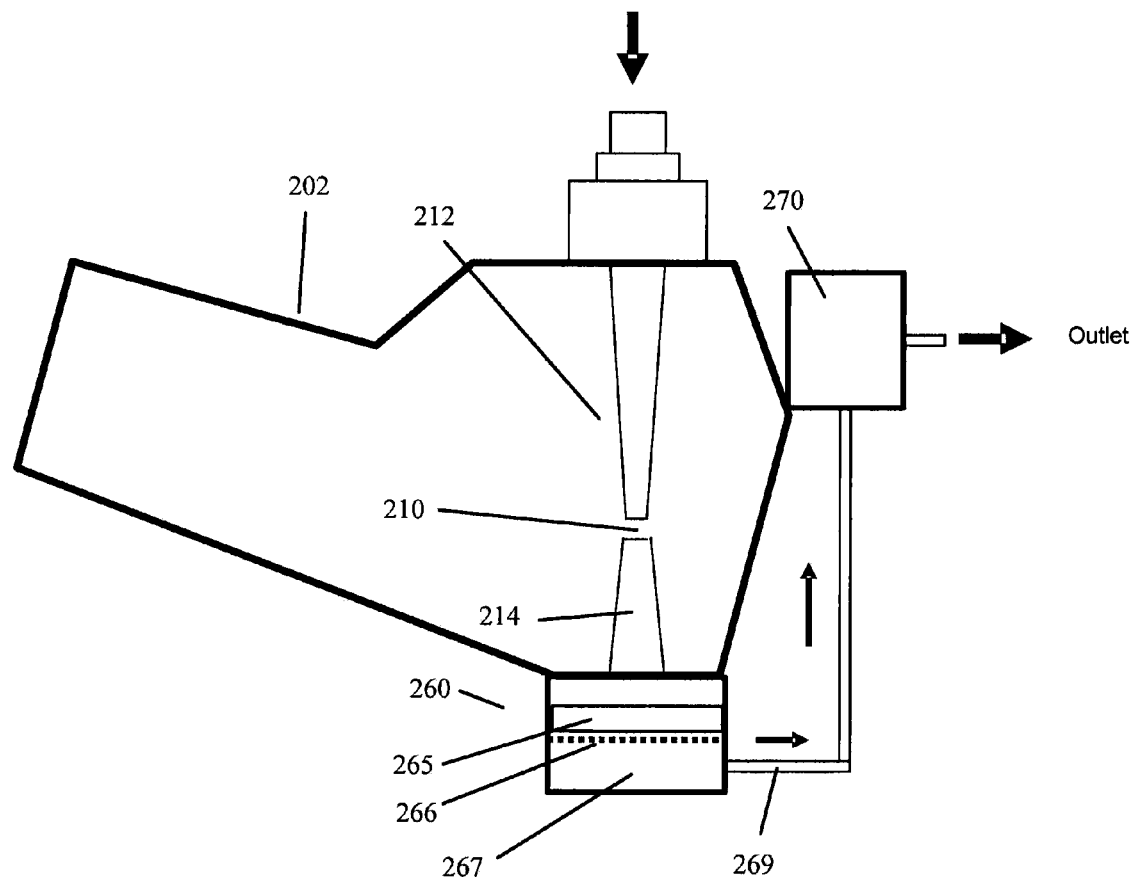
FIG. 2 is a schematic diagram showing the microbial collector components of a particle sizing and biological detection system according to an embodiment of the invention in additional detail.

FIG. 2 shows the microbial collection components of a system according to an embodiment of the invention. In certain embodiments, the microbial collection components illustrated in FIG. 2 are used with the optical sizing and biological detection components described in reference to FIG. 1. FIG. 2 omits the optical components for clarity, however. The system of FIG. 2 includes a housing 202. In the system of FIG. 2, air to be measured is routed to a sampling area 210 via an entrance nozzle 212. Once in sampling area 210, particles in the air are sized and classified as biological or non-biological by measuring the angular distribution of scattered light and fluorescence. One exemplary way this is accomplished by the operation of system components described above with respect to FIG. 1. After being measured optically in sampling area 210, air being measured is extracted from sampling area by exit nozzle 214 where it is passed to filter holder 260.

Filter holder 260 contains microbe collection filter 265. In one embodiment, microbe collection filter 265 is a 47 mm gelatin plate that can be removed from filter holder 260 and placed in a conventional Petri dish for incubation. Microbe collection filter 265 has a front side facing toward exit nozzle 214 and a rear side facing toward perforated support plate 266, which itself includes perforations allowing fluid flowing through microbe collection filter 265 to flow the perforations into a rear chamber 267 of filter holder 260. Rear chamber 267 is in fluid communication with exit fluid line 269. Microbe collection filter 265 is supported by perforated support plate 266, which includes a plurality of perforations allowing fluid to flow from the back side of the microbe collection filter 265 through the support plate 266. Filter holder 260 is configured to provide an air-tight seal, by the use of compressed o-rings or the like, such that substantially all of the air extracted from sampling area 210 through exit nozzle 214 flows through the microbe collection filter 265. From the back side of microbe collection filter 265, air flows through the perforations in support plate 266, and through fluid exit line 269, which is in fluid communication with blower 270. Blower 270 draws fluid through exit line 269, the perforations in support plate 266, and microbe collection filter 265. Since microbe collection filter 265 and its support plate provide a partial obstruction to air flow, the suction created by blower 270 at the front side of microbe collection filter 265 will be less than the suction created by blower 270 near the back side of microbe collection filter 265. The suction at the back side of microbe collection filter 265 is maintained at a level sufficient to extract the air being measured from sampling area 210. This is accomplished by selecting sufficiently high blower suction, and a sufficiently high cross-sectional perforation area of the gelatin filter's support plate to maintain adequate negative pressure at the exit nozzle 214.

In one embodiment, microbe collection filter 265 is a gas-permeable substance that causes microbial particles in fluid exposed to the filter to adhere to the filter. Additionally, microbe collection filter 265 is configured to maintain microbial viability so that microbes collected by the filter can be cultured and analyzed. In particular embodiments, microbe collection filter 265 is a gelatin wafer having a sufficiently high water content to maintain microbial viability, although the use of gelatin is not a requirement. Any filter containing a gas permeable substance with a high moisture content to maintain biological viability, to which microbes present in fluid exposed to the filter adhere, is acceptable to use as the filter described herein.

In the embodiment of FIG. 2, microbial collection filter 265 is removable so that, after a measurement period, the microbe collection filter 265 can be incubated and then analyzed to determine the number, and in certain embodiments, the types of microbes that were present in the measured air during the measurement period. In an exemplary process, after exposure, microbial collection filter 265 is removed and covered with a sterile cover for transport. After transport, microbial collection filter 265 is placed in contact with a growth medium containing plate, e.g., an agar containing Petri dish. The filter is then incubated for some amount of time, and the resulting microbial growth is analyzed. Analysis can take several forms. For example, microbial colonies may be visually visible and can be counted to determine the number of microbes that landed on the microbial collection filter during the measurement period. Additional analyses may be performed, for example, in certain cases the shape, i.e., the macroscopic appearance, of a microbial colony can provide information about the type of microbe present. Additionally or alternatively, microscopic observation of the microbes, chemical testing for the metabolic by-products of microbial growth and/or DNA analysis can determine the type of microbe collected.

Figure 3:
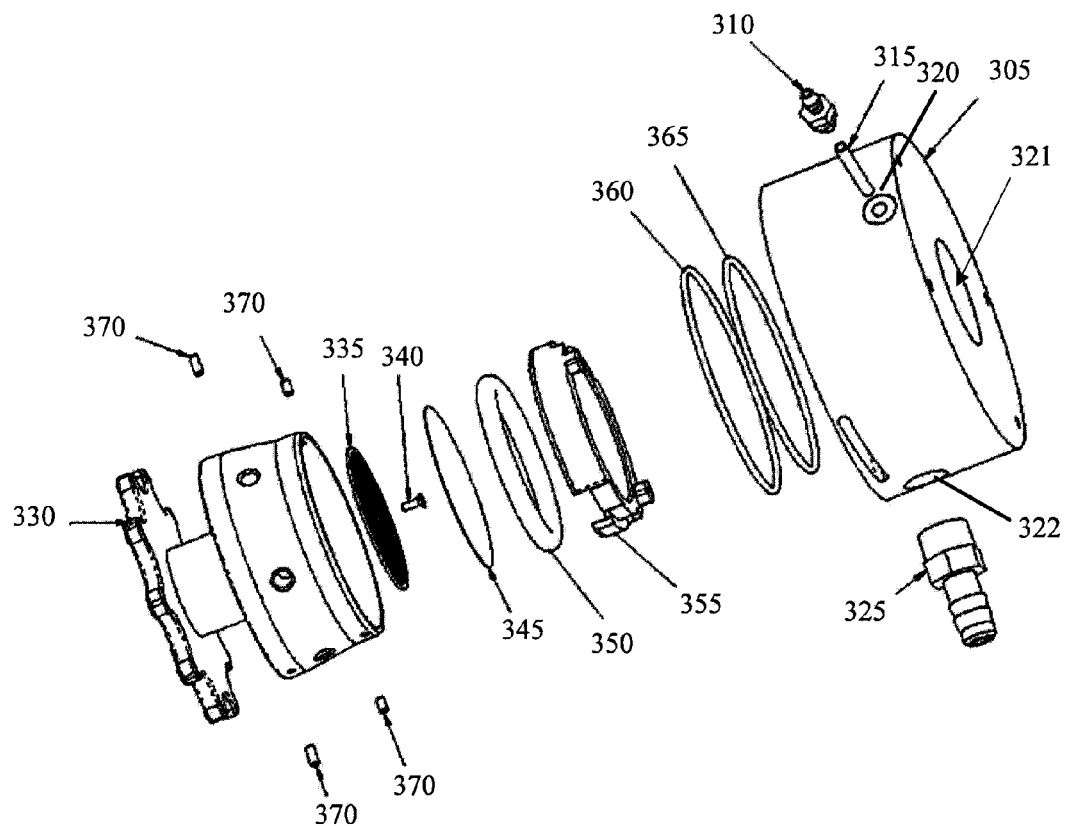
FIG. 3 is an exploded drawing showing an assembly for holding a microbe collection filter according to an embodiment of the invention.

FIG. 3 is an exploded drawing showing a microbe collection filter assembly according to an embodiment of the invention. FIG. 3 shows a preferred embodiment for the filter holder 260 described above with respect to FIG. 2. Microbe collection filter assembly includes cartridge housing 305. Cartridge housing 305 includes hose barb 310 and flow sensor tube 315 which are arranged at sensor input aperture 320 one the side of the cartridge housing. This sensor assembly can be used to monitor air flow by the Venturi effect or the like. Fluid exiting the system enters cartridge housing, and therefore filter assembly, via input aperture 321 which is in fluid communication with an exit nozzle of the system, for example, exit nozzle 214 described above with FIG. 2. After being extracted from the sampling area of the system, fluid is routed into cartridge housing 305 via, for example, a non-illustrated hose attached to hose part 310. Cartridge housing 305 also includes output aperture 322 and hose barb 325. Fluid under test passes through output aperture 322 to non-illustrated blower after passing through microbe collection filter, which is described in additional detail below.

The assembly of FIG. 3 includes cartridge 330, which includes a knurled handle for easier handling. The function of cartridge 330 is to hold a microbe collection filter in cartridge housing 305 such that the microbe collection filter is sealed in the flow path of fluid being extracted from the system. Cartridge 330 includes support plate 335. Support plate 335 is, in one embodiment, a rigid disk containing perforations that allow fluid flow. An illustrative embodiment of support plate 335 is set forth in more detail below with respect to FIG. 4.

Support plate 335 is secured to cartridge 330 by a fastener 340 that engages a through-hole in support plate 335.

The assembly of FIG. 3 includes microbe collection filter 345. In one embodiment, microbe collection filter is a disk of gas-permeable, water impregnated gelatin, but this is not a requirement. Microbe collection filter need only be capable of trapping some microbes present in air to which microbe collection filter 345 is exposed. Microbe collection filter is secured into cartridge 330 with o-ring 350 and clamp ring 355. Once assembled cartridge 330 is inserted into and sealed against cartridge housing 305 with additional o-rings 360, 365. Cartridge 330 is secured in cartridge housing 305 using a plurality of pins 370. Upon assembly microbe collection filter 345 is sealed in the fluid flow path emerging from the system such that all of the fluid emerging from the system is forced through microbe collection filter 345.

Figure 4:
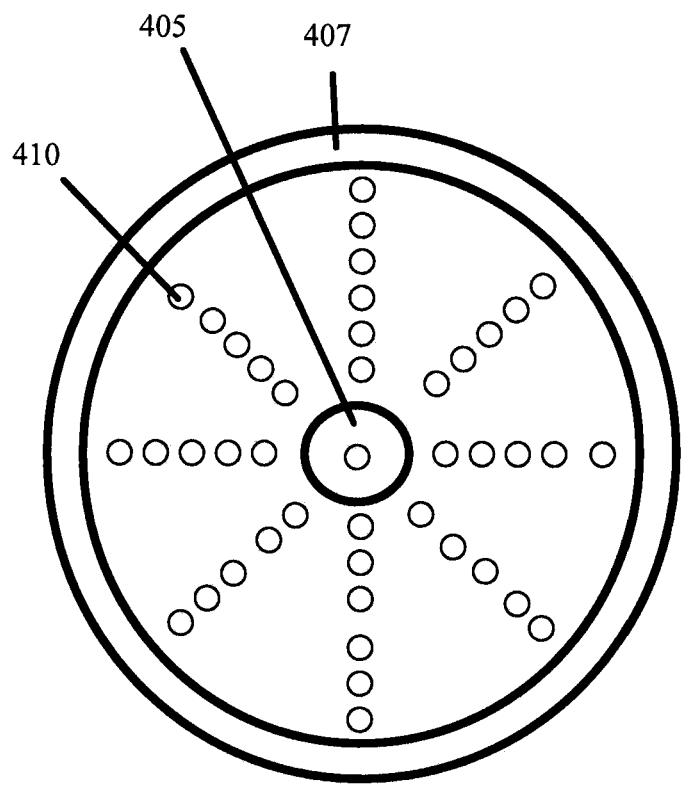
FIG. 4 is a plan view of an exemplary filter support plate suitable for use in conjunction with an embodiment of the invention.

FIG. 4 shows an exemplary filter support plate suitable for use in conjunction with an embodiment of the invention. In one embodiment, filter support plate is approximately 47 mm in diameter. The filter support plate of FIG. 4 includes a central aperture 405 having a diameter of approximately 3 mm. Central aperture 405 is optionally chamfered to receive a non-illustrated fastener. Filter support plate includes an outside annular zone 407, configured to lay outside the area of microbe collection filter beings supported by the filter support plate. Outside annular zone 407 is optionally used for mounting or sealing to the filter support plate. In one embodiment, the filter support plate of FIG. 4 is approximately 1 mm thick.

The filter support plate of FIG. 4 includes a plurality of perforations 410 that allow air to flow from front to back. Although circular, radially arranged perforations are shown with respect to the filter support plate of FIG. 4, this not a requirement. The only requirement is that the filter support plate includes perforations sufficient to allow air to flow through a gas-permeable microbe collection filter, e.g., a gelatin wafer, in contact with the filter support plate while mechanically supporting the microbe collection filter against deformations caused by air pressure.

Figure 5:
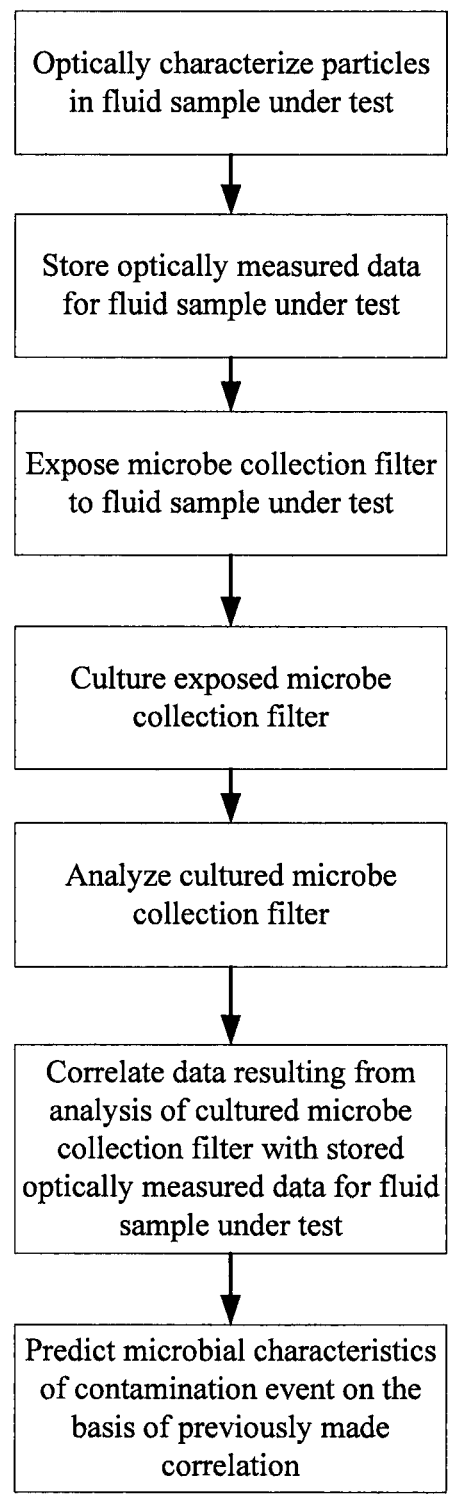
FIG. 5 is a schematic flowchart illustrating steps of a method of microbial detection and analysis according to an embodiment of the invention.

FIG. 5 shows a method of detecting and identifying microbes according to an embodiment of the invention. In the method of FIG. 5 particles in a fluid under test, for example air, are optically characterized. Optical characterization is conducted by illuminating the fluid under test with a beam of light, for example a beam of light generated by a laser or LED emitting at a wavelength of between 270 nm and 410 nm. Particles present in the fluid scatter light by Mie scattering at various angles depending on the size of the scattering particle. Additionally, biological particles in the fluid absorb light and re-radiate light at longer wavelengths by fluorescence. Light that is scattered into predetermined angles by particles in the fluid is detected and used to determine the size of the scattering particles. At the same time, light emitted by fluorescence from the particles is detected and used to make a determination as to whether the particles are biological or non-biological. The scattered light and fluorescence measurements are temporally correlated to determine the size of biological and non-biological particles present in the fluid being measured. Additionally, the scattered light and fluorescence measurements are stored, for example as a function of time, for later use and analysis.

After the fluid being measured is optically characterized, that fluid is exposed to a gas-permeable microbe collection filter, e.g., a gelatin wafer. After a predetermined period of time, the gas-permeable microbe collection filter is removed and cultured to encourage microbial growth. The culturing process comprises providing nutrients to microbes on the exposed gas-permeable microbe collection filter, and incubating same. After an incubation period has elapsed, the cultured microbe collection filter is analyzed. Such analysis can occur by any number of means, for example, colony counting, observing the macroscopic appearance of the growth patterns of microbes on the filter, microscope observation of the microbes, chemical testing for the metabolic by-products of microbial growth, or DNA testing.

If the analysis applied to the incubated filter determines the number of microbes that were present in the filter after the exposure period, this number is, in one embodiment, correlated with the optically measured data on the size and number of biological particles detected during the exposure period. Accordingly, correlating the optically measured data with the data from analysis of the cultured filter can be as simple as comparing the microbe count from the filter with the number of optically detected particles.

If the analysis applied to the incubated filter determines the types of microbes present on the filter at the time of exposure, this information, in one embodiment, is correlated with the stored data on the size and biological status of particles measured optically at the time the filter was exposed. This correlation optionally results in a determination of the number and types of microbes present in the fluid sample during the measurement period, i.e., the period of time the filter was exposed to fluid for which optical data was collected. This determination is made with the aid of conventional knowledge of the size of the types microbes identified on the filter by the analysis of the incubated filter.

The method illustrated in FIG. 5 has a number of advantages. First, the method of FIG. 5 provides a more complete retrospective characterization of the measured fluid sample by including information about the type of microbes that were instantaneously detected. Second, data collected according to the method of FIG. 5 allows for tentative, real-time characterization of future biological contamination events based on previously measured data. For example, suppose a contamination event occurs that results in numerous biological particles in the 0.4-0.8 µm range, which are instantaneously detected by the optical systems and methods set forth above. Upon analysis of a growth-medium containing filter exposed to air measured during this hypothetical contamination event, it is determined that most of these biological particles were a particular kind of microbe. In the future, whenever a spike of biological particles in the 0.4-0.8 µm range is detected under similar conditions, it can be assumed that another contamination event associated with the previously detected microbe is occurring in the monitored environment, and a real-time response appropriate to that contamination event can be coordinated. A predictive step is illustrated in FIG. 5, where microbial characteristics of a contamination event are predicted by matching optically collected data with previously optically collected data that was previously correlated to a particular set of identified microbes.

Figure 6:
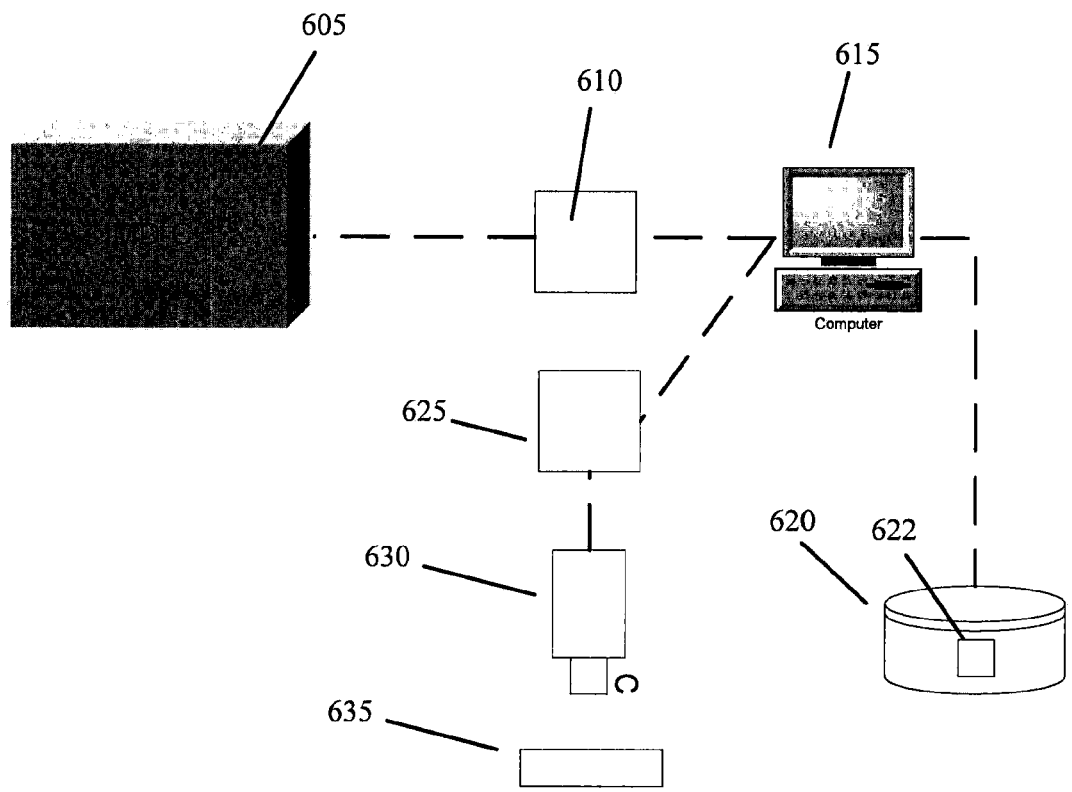
FIG. 6 is a schematic block diagram of a computer-automated machine vision and analysis system according to an embodiment of the invention.

Computer hardware, software and machine vision components can be used to perform, assist or simplify and of the process steps performed herein. FIG. 6 shows an exemplary computer system for performing analysis of a fluid under test according to an embodiment of the invention. The system of FIG. 6 includes a particle sizing, biological particle identification, and microbial collection system 605. In certain embodiments, system 605 is the system described above with respect to FIGS. 1 and 2. System 605 performs real-time particle detection and sizing as well as real-time determination of whether detected particles are biological or non-biological. Additionally, system 605 performs microbial collection by exposure of a microbe collection filter to the fluid being optically measured. The optically measured data is converted to electrical signals by electronics included with system 605, for example, by the drive electronics associated with a photo-diode measuring optical scattering and a PMT measuring fluorescence light. The electrical signals generated by these two detectors are transmitted from system 605 to optional computer data acquisition card 610, which is electronic communication with computer 615. Optically measured data is then stored in a persistent storage medium, for example, hard disk 620.

The system of FIG. 6 further includes machine vision camera 630, which is electronic communication with image capture board 625, which in turn is in electronic communication with computer 615. After a microbe collection filter 635 has been incubated, and microbial colonies are visible, camera 630 captures an image of the colonies visible on filter 635. To assist in this task, optional non-illustrated steppers may be used to translate the field of view of camera 630 with respect to filter 635 or vice-versa. An image or images of the filter showing microbial colonies is stored by computer 615 to disk 620.

Disk 620 also includes computer readable instructions 622 operable to cause computer 615 to correlate and/or compare the colony count detected by camera 630 with the optically measured data regarding the number and biological or non-biological status of particles measured during the time period when filter 635 was exposed. More generally, embodiments of the invention include instructions, such as instructions 622, residing in computer readable medium, such as for example computer hard drive 620 wherein those instructions are executed by a processor, such as processor residing in computer 615, to perform one or more of steps illustrated with respect to FIG. 5, for example the storage step, analyze step, correlate step or predict step. Computer readable instructions 622 need not reside on hard disk 620, but may reside in any medium capable of being in electronic communication with a processor capable of executing instructions 622. For example, there is no requirement that data (e.g., optically measured particle data) be stored on the same medium that includes instructions 622. Additionally, while FIG. 6 shows computer 620, camera 630 and other components being separate from system 605, this is not a requirement. System 605 could be configured to include a microprocessor, storage, memory, input/output electronics and a camera necessary to perform the method steps described herein.

In other embodiments, Applicants' invention includes instructions residing in any other computer program product, where those instructions are executed by a computer external to, or internal to, systems such as system 605, to perform one or more steps described with respect to FIG. 5. In either case, the instructions may be encoded in computer readable medium comprising, for example, a magnetic information storage medium, an optical information storage medium, an electronic information storage medium, and the like. By "electronic storage media," Applicants mean, for example and without limitation, one or more devices, such as and without limitation, a PROM, EPROM, EEPROM, Flash PROM, compactflash, smartmedia, and the like.

While the preferred embodiments of the present invention have been illustrated in detail, it should be apparent that modifications and adaptations to those embodiments may occur to one skilled in the art without departing from the scope of the present invention as set forth in the following claims.

What is claimed is:

1. A microbial detection and identification system, comprising:

a housing, including a sampling area having a fluid, a light source, a first optical detector and a second optical detector;

a blower in fluid communication with said housing, wherein said blower supplies negative pressure to said housing thereby drawing environmental air into said sampling area and evacuating air from said sampling area;

a microbe collection filter in fluid communication with said sampling area, wherein environmental air is drawn by the blower from said sampling area through the microbe collection filter, and a perforated support plate in contact with a rear side of the microbe collection filter.

2. The system of claim 1, wherein said sampling area is defined by an input nozzle and an output nozzle.

3. The system of claim 2, wherein said microbe collection filter includes a front side facing said exit nozzle, a rear side in fluid communication with said blower, and a gas permeable interior allowing said fluid to flow into said front side and out of said rear side.

4. The system of claim 1, wherein,
said light source illuminates particles in said sampling area,
said first detector detects light scattered into a predetermined angular range by particles of a predetermined size,
said second detector measures light emitted by fluorescence from illuminated biological particles in said sample area,
and said fluid is exposed to said microbe collection filter causing particles in said fluid to adhere to said microbe collection filter.

5. The system of claim 4, further comprising scattered light collection components that direct scattered light from said sampling area to said first detector and a plurality of optical components that direct fluorescence light from said sampling area to said second detector.

6. The system of claim 5, wherein said plurality of optical components includes a long-pass filter that selectively transmits light having a wavelength of light emitted by fluorescence by illuminated particles in said sample area.

7. The system of claim 6, wherein said long-pass optical filter comprises two long-pass reflective filters in series.

8. The system of claim 5 further comprising an ellipsoidal reflector having a first focus at said sampling area and a second focus near said second detector.

9. The system of claim 1, wherein said light source comprises an LED or a diode laser, and wherein said light source emits at a wavelength of approximately between 350 nm and 410 nm.

10. The system of claim 1, wherein said blower is in fluid communication with said microbe collection filter, and wherein air is drawn through said microbe collection filter after it is optically measured.

11. The system of claim 1 wherein said microbe collection filter comprises a gelatin wafer.

12. The system of claim 1, wherein said microbe collection filter has a front side arranged transverse to the flow of fluid being measured.

13. A microbe collection filter for use with a microbial detection and identification system, the system having a housing, including a sampling area having a fluid, a light source, at least one optical detector, and a blower in fluid communication with said housing, wherein said blower supplies negative pressure to said housing thereby drawing environmental air into said sampling area evacuating air from said sampling area;

the microbe collection filter having a front side, a rear side, and a fluid-permeable interior, wherein the microbe collection filter is arranged transverse to the flow of fluid being measured, wherein the microbe collection filter is supported by a perforated support plate in contact with the rear side of the microbe collection filter, and wherein the perforated support plate is arranged between the microbe collection filter and the blower.

14. A microbial detection and identification system comprising:

a housing, including a sampling area having a fluid, a light source, at least one optical detector, and a blower in fluid communication with said housing, wherein said blower supplies negative pressure to said housing thereby drawing environmental air into said sampling area evacuating air from said sampling area;

a removable cartridge housing a microbe collection filter having a front side, a rear side, and a fluid permeable interior volume, and an input aperture arranged transverse to the flow of fluid being measured in fluid communication with both the sampling area and the front side of the microbe collection filter, wherein the cartridge includes a perforated support plate in contact with the rear side of the microbe collection filter, and an output aperture arranged between the rear side of the microbe collection filter and the blower.

* * * * *